United States Patent [19]

Jones et al.

[11] 4,046,760

[45] Sept. 6, 1977

[54] PROCESS FOR PREPARING 1-α-HYDROXY CHOLESTEROL DERIVATIVES

[75] Inventors: Howard Jones, Holmdel; Robert A. Frankshun, Plainfield, both of N.J.

[73] Assignee: Merck & Co., Inc., Rahway, N.J.

[21] Appl. No.: 701,917

[22] Filed: July 1, 1976

[51] Int. Cl.² .............................................. C07J 21/00
[52] U.S. Cl. ........................ 260/239.55 R; 260/397.2
[58] Field of Search ........................ 260/397.2, 239.55

[56] References Cited

U.S. PATENT DOCUMENTS

| | | | |
|---|---|---|---|
| 3,901,928 | 8/1975 | Hesse et al. | 260/239.55 |
| 3,901,928 | 8/1975 | Hesse et al. | 260/397.2 |
| 3,929,770 | 12/1975 | Ishikawa et al. | 260/239.55 |
| 3,966,777 | 6/1976 | Mazur et al. | 260/397.2 |

*Primary Examiner*—Elbert L. Roberts

[57] ABSTRACT

Improved processes are described for introducing a 1-α-hydroxy group into the cholesterol ring system. Novel intermediates and their preparation are disclosed.

6 Claims, No Drawings

PROCESS FOR PREPARING 1-α-HYDROXY CHOLESTEROL DERIVATIVES

The instant invention may be described as residing in the concept of a new and useful process for preparing 1α-hydroxy cholesterol derivatives, to novel intermediates therein and to the process for preparing such intermediates. The 1α-hydroxy cholesterol derivatives prepared by the novel process of the instant invention are readily converted, by techniques already well-known in the art, into the corresponding 1α-hydroxy 9,10-secosteroids, such as 1α-hydroxy-cholecalciferol, which are useful therapeutic agents in the treatment of human and non-human arthritic conditions (see Housslar et al., "Biological Activities of 1α-Hydroxy Cholecalcifero, A Synthetic Analog of the Hormonal Form of Vitamin $D_3$", Proc. Nat. Acad. Sci. U.S.A., Vol. 70, No. 8, pp 2248–2252, August 1973).

The instant invention is based upon applicants discovery that the 1α-hydroxy group may be introduced into the cholesterol ring system by a novel synthetic route in good yield and with a minimum of purification steps. The 1α-hydroxy cholesterol derivatives prepared by the novel process of the instant invention have the following structure formula:

VI

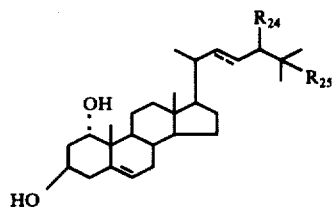

wherein $R_{24}$ is a member selected from the group consisting of hydrogen and methyl and $R_{25}$ is a member selected from the group consisting of hydrogen and hydroxy.

The overall process according to the instant invention is illustrated by the following flow sheet, wherein the substituents $R_{24}$ and $R_{25}$ have the significance indicated in formula VI above, and in the accompanying description of the individual steps therein. The starting materials are known compounds, either available commercially or readily prepared by processes already fully described in the literature.

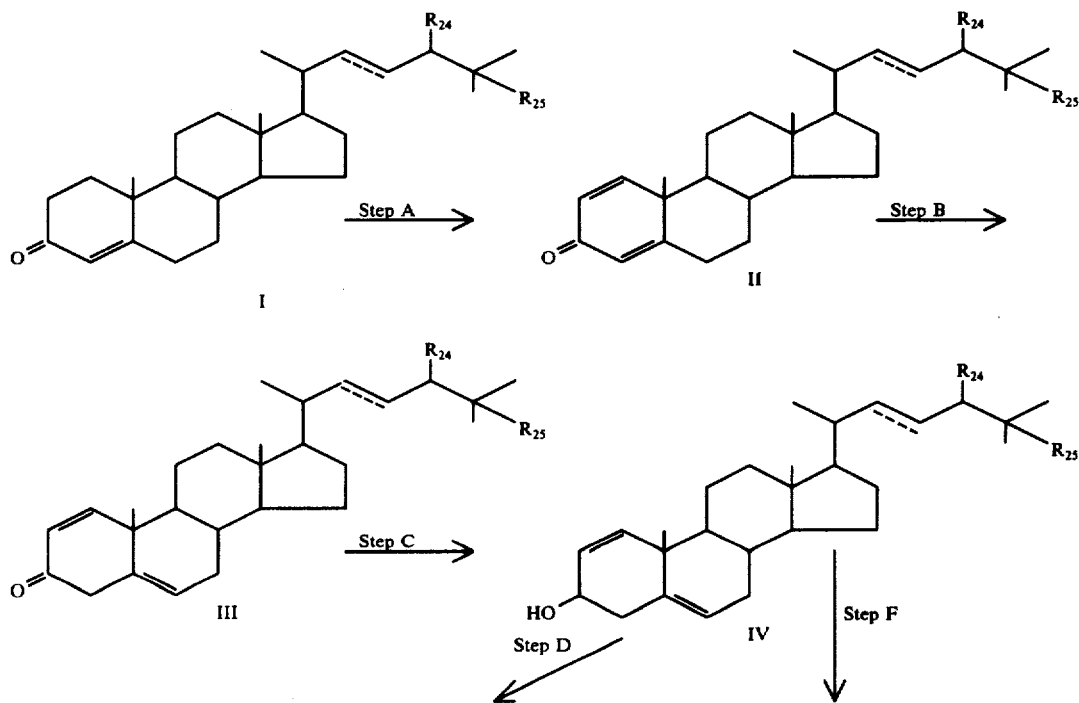

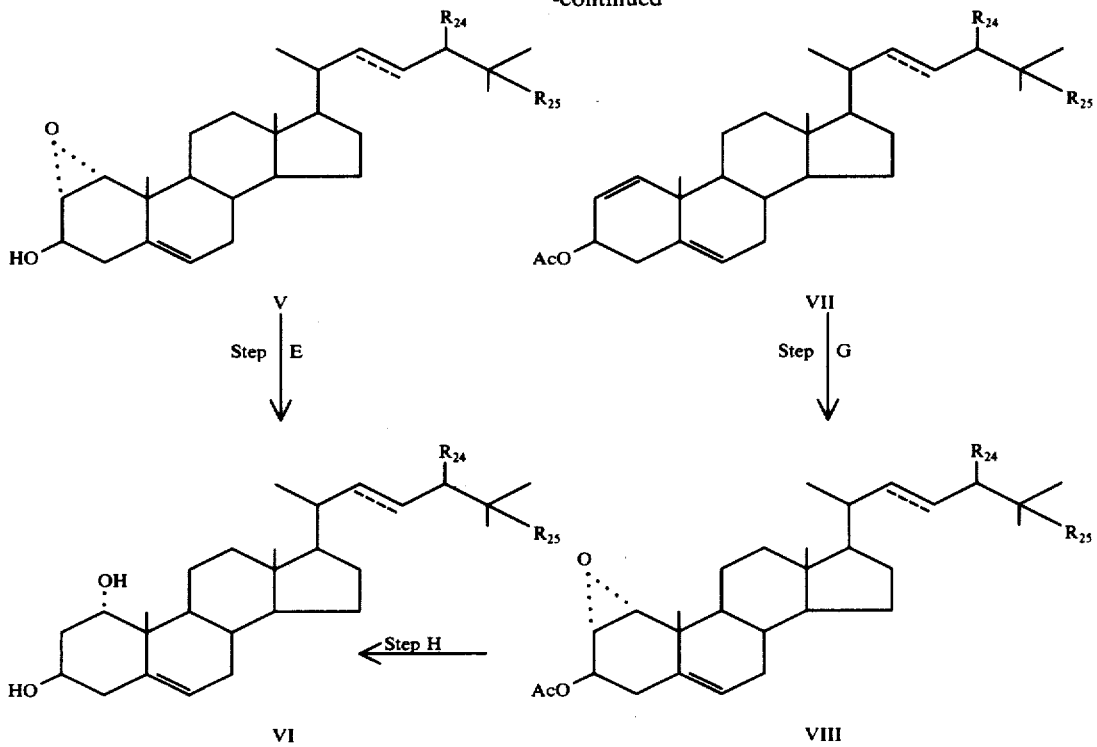

STEP A — DEHYDROGENATION OF THE 3-KETO-Δ⁴ SYSTEM

Dehydrogenation of the 3-keto-Δ⁴-starting material (compound of formula I) may be carried out by treating the starting material with 1.0 to 1.5 moles, preferably 1.1 to 1.25 moles, of 2,3-dichloro-5,6-dicyano-1,4-benzoquinone (DDQ) in a suitable organic solvent. Typical solvents include, for example, hydrocarbons having boiling point of 70° to 120° C., such as benzene, toluene, cyclohexane and the like, or mixtures thereof. The reaction, conveniently, is carried out in an open system at atmospheric pressure and at reflux temperature. The reaction is usually complete in 4 to 24 hours. Upon completion of the reaction, the reaction mixture is filtered and concentrated in vacuo and the crude product is worked-up by conventional chromatographic techniques using a silica-gel column and eluting agents such as benzene and mixtures thereof with ethyl actate. Concentration of the appropriate fraction followed by recrystallization yields the desired 3-keto-Δ¹,⁴-product (the compound of formula II)

Alternatively, dehydrogenation may be accomplished by selectively halogenating the starting 3-keto-Δ⁴-compound with a suitable halogenating agent, such as bromine or chlorine, followed by dehydrohalogenation with a 50/50 molar mixture of lithium bromide and lithium carbonate. The reaction may be carried out at reflux in solvents such as ether, chloroform, tetrahydrofuran, dimethylformamide, benzene and the like and usually is completed in 2 to 4 hours. Conventional work-up yields the desired diene.

STEP B — REARRANGEMENT OF THE 3-KETO-Δ¹,⁴-SYSTEM TO FORM THE 3-KETO-Δ¹,⁵-SYSTEM

Rearrangement of the 3-keto-Δ¹,⁴-compound obtained above may be carried out in the presence of proton abstracting bases in suitable solvents. Such proton abstracting bases include, for example, $C_{1-5}$ alkoxides such as potassiumtert-butoxide, sodium ethoxide, potassium methoxide, sodium isopropoxide and the like, with the corresponding $C_{1-5}$ alkanol or dimethyl sulfoxide being employed as the solvent; sodium hydride and alkali and alkaline earth metals such as potassium, sodium, lithium and calcium, with ethers such as dimethyl ether, tetrahydrofuran, dimethyl formamide, dioxane and the like and aromatic hydrocarbons such as benzene and toluene being employed as the solvent; and lithium diisopropamide using liquid ammonia as the solvent. The reaction temperature is not critical. Generally, the reaction is carried out at temperatures between about −80° C. to the reflux temperature of the solvent. Reaction temperatures between about 0° C. are preferred. The reaction is rapid and usually is complete in 45 minutes to 2 hours. After the reaction is completed, the reaction mixture is poured with stirring into water containing a weak acidifying agent which is chilled to about 0° C. to about 10° C. Suitable weak acidifying agents include ammonium chloride and carbonic acid which may be prodiced by saturating the water with carbon dioxide. The desired 3-keto-Δ¹,⁵-product, the compound of formula III, is recovered from the reaction mixture by extraction using solvents such as diethyl ether, diisopropyl ether, benzene, chloroform, methylene chloride and the like. The extracted product then is recovered by conventional techniques and, if desired, may be further purified by chromatography over silica-gel.

STEP C—REDUCTION OF THE KETO GROUP

Reduction of the 3-keto group of the 3-keto-Δ¹,⁵-compound produced above in order to obtain the 3-hydroxy-Δ¹,⁵-compound of formula IV is carried out be dissolving the 3-keto-Δ¹,⁵-compound in a suitable solvent and treating the solution with a reducing agent capable of reducing the ketone group to a hydroxy group. Suitable reducing agents include lithium borohydride, sodium borohydride, lithium (tri-t-butoxy) aluminumhydride, potassium borohydride, diborane ($B_2H_6$), calcium borohydride and lithium aluminium hydride. Suitable solvents include ethers such as ethyl ether, tetrahydrofuran, dioxane, or diethylether, aromatic hydrocarbons such as benzene, aliphatic hydrocarbons such as hexane and cyclohexane and water (limited to use with sodium borohydride). The reaction, conveniently, is carried out at room temperature although temperatures between about 0° C. and the reflux temperature of the solvent are suitable. Reaction usually is complete in 1 to 8 hours. Upon completion of the reaction, excess reducing agent is destroyed by the addition of water or a reactive ester such as ethyl acetate. The desired product may be recovered by separating and concentrating the solvent and, if desired, may be further purified by chromatography over silica-gel.

STEP D—EPOXIDATION

The 3-hydroxy-$\Delta^{1,5}$-product of the preceding step then is epoxidized with 1.0 to 1.5 moles, preferable 1.1 to 1.25 moles, of a suitable oxidixing agent in a suitable solvent at a temperature between about 0° C. and the reflux temperature of the solvent. Suitable oxidizing agents include sodium chlorate, peracids such as peracetic acid trifluoroperacetic acids and perbenzoic acid, and hydrogen peroxide. Suitable solvents include, i.e., water for the hydrogen peroxide, the corresponding organic acid for the peracids, halogenated $C_{1-2}$ alkanes such as chloroform and methylene chloride and aromatic hydrocarbons such as benzene and toluene. The reaction is carried out in an open system at atmospheric pressure and usually is complete in 1 to 2 hours. The oily epoxide product, the compound of formula V, may be recovered by concentrating the reaction mixture and may be further purified by chromatography over silica-gel.

The 1$\alpha$,2$\alpha$-epoxy-$\Delta^5$-cholestene-3$\beta$-01 compounds produced by this technique, and the corresponding 3$\beta$-acetates produced in Step F below, are novel compounds and constitute the composition of matter aspect of the instant invention.

STEP E—REDUCTION OF THE EXPOXIDE GROUP

Reduction of the epoxy group of the product of the preceding step in order to obtain the 1$\alpha$hydroxy cholesterol derivative of formula VI is carried out by dissolving the epoxy compound in a suitable solvent and treating the solution with a reducing agent capable of reducing the epoxide group to a hydroxy group. Suitable reducing agents include, for example, calcium borohydride, lithium aluminum hydride, potassium borohydride, lithium in triethyl amine, sodium in $C_{1-3}$ alkanols such as methanol, ethanol and propanol, catalytic hydrogenation using a noble metal catalyst as a platinum oxide or nickel, and finely divided metallic zinc in acetic acid. Suitable solvents include, for example, aromatic hydrocarbons such as benzene and toluene, aliphatic hydrocarbons such as hexane and cyclohexane and ethers such as tetrahydrofuran, dioxane and diethyl ether. The reaction may be carried out between 0° C. and the reflux temperature of the solvent. Preferably at room temperature, and usually is complete in 4 to 6 hours. Upon completion of the reaction, excess reducing agent is destroyed by the addition of water or a reactive ester such as ethylacetate and the desired product is obtained by concentration of the solvent. Purification may be achieved by chromatography over silica-gel.

As will be noted from the foregoing flow sheet, the process of the instant invention also contemplates an altenative synthetic route involving acetylation of the 3-hydroxy-$\Delta^{1,5}$-compound of formula IV to form the 3-acetoxy-$\Delta^{1,5}$-compound of formula VII followed by epoxidation to form the epoxy compound of formula VIII and reduction to form the 1$\alpha$-hydroxy cholesterol derivative of formula VI. These steps are described in greater detail below.

STEP F—ACETYLATION OF THE 3-HYDROXY -$\Delta^{1,5}$-SYSTEM

Acetylation of the 3-hydroxy-$\Delta^{1,5}$-compound obtained in STEP C above is carried out by treating the the 3-hydroxy-$\Delta^{1,5}$-compound with an excess of acetic anhydride (5 to 50 moles of acetic anhydride per mole of 3-hydroxy-$\Delta^{1,5}$-starting material) in a suitable solvent and in the presence cf an acid acceptor such as pyridine at a temperature between about $-20°$ to about $+20°$ C., preferrably at $-20°$ to $0°$ C. Suitable solvents include, for example, triethylamine, piperidine, dimethylformamide and the like. The reaction mixture is allowed to warm slowly to room temperature and usually is allowed to age overnight. The desired 3-acetoxy-$\Delta^{1,5}$-product, the compound of formula VII, is recovered by concentrating the reaction mixture, extraction with a suitable solvent such as chloroform and crystallization.

It will be obvious to those skilled in the art that, if desired, esters other than the acetate such as the propionate and benzoate could be formed merely by selecting the appropriate anhydride reactant.

STEP G—EPOXIDATION

STEP H—REDUCTION

The epoxidation of the 3-acetoxy-$\Delta^{1,5}$-product of the prededing step to form the epoxy acetate compound of formula VIII and the reduction thereof to form the desired 1$\alpha$-hydrooxy cholesterol derivative of formula VI are carried out in the manner already described in STEP D and STEP E above. It will be noted that the reduction simultaneously removes the epoxide group and converts the acetoxy group to hydroxy. The best mode contemplated by applicants for carrying out the process of the instant invention is illustrated in the following working examples, no limitation being intended except as set forth in the appended claims.

EXAMPLE I

Preparation of 1$\alpha$-Hydroxycholest-5-enol

A. Preparation of $\Delta^{1,4}$-Cholestedien-3-one $\Delta^4$-Cholestene-3-one, (20 g or 0.052 moles), is dissolved in benzene (180 ml.). To this is added with stirring, 2,3-dichloro-5,6-dicyano-1,4-benzoquinone, (15.5 g or 0.068 moles). The mixture is refluxed for 4½hours and at the end of this time a thin layer chromatography plate run in 20% ethyl acetate/benzene indicates that the starting material has disappeared. The reaction mixture is filtered and concentrated in vacuo and the crude product is worked up by chromatography on silica-gel column and eluted with benzene and mixtures thereof with ethyl actate. Concentration of the appropriate fraction followed by recrystallization from benzene yields 18 g. of $\Delta^{1,4}$-cholestediene-3-one, melting point 111° C.

B. Preparation of $\Delta^{1,5}$-Cholestediene-3-one $\Delta^{1,4}$-Cholestediene-3-one (1 g or 0.0026 moles) prepared according to Example IA above is dissolved in 10 ml. of dry dimethyl sulfoxide. To this, with stirring and cooling, is added potassium-t-butoxide (0.59 g. or 0.0052 moles). The reaction mixture is stirred for 2 hours and then poured into 100 ml. of ice-water saturated with carbon dioxide. The crude product is extracted with methylene chloride, dried filtered and concentrated under vacuum to yield a yellow oily solid. The crude product is used as in the next reaction (or it can be chromatographed on silica-gel mixtures of benzene and ethyl acetate). Concentration of the appropriate cut yields 0.75 g. of the desired $\Delta^{1,5}$-cholestediene-3-one. The $\Delta^{1,5}$-cholestediene-3-one has the characteristic nuclear magnetic resonance spectrum and is pure by thin layer chromatography. Melting point 108°–110° C.

C. Preparation of $\Delta^{1,5}$-Cholestediene-3$\beta$-ol

The ketone prepared according to Example IB above, (200 mg. or 0.0005 moles) is dissolved in dry ether (15 ml.) and added dropwise to a slurry of lithium aluminum hydride (20 mg. or 0.005 moles) in ether (10 ml.) with cooling. The reaction mixture is stirred for 1 hour and then 1 ml. of ethyl acetate is slowly added to decompose the excess lithium aluminum hydride. The reaction mixture is shaken with saturated ammonium chloride solution, and the ether layer washed with water and saturated becarbonate solution. The ether layer is dried, filtered and concentrated to a white solid. Thin layer chromatography of this solid using benzene: 20% ethyl acetate showed that no starting material that no starting material remained. The crude product is used as is in the next reaction, or can be chromatographed to purity using mixtures of benzene/ethyl acetate acetate as illustrated. In this way 160 mg. of pure material, melting point 122–125° C., with the correct nmr spectrum.

D. Preparation of 1$\alpha$,2$\alpha$-Epoxy-$\Delta^5$-Cholestene-3$\beta$-ol $\Delta^{1,5}$-Cholestediene-3$\beta$-01, prepared according to Example IC, above (710 mg. or 0.00185 moles) is dissolved in dry chloroform (25 ml.) and cooled to 0° in an ice bath. M-Chlorperbenzoic acid (413 mg. or 0.002 moles) dissolved in chloroform (25 ml.) is added dropwise to this mixture with stirring. The reaction mixture is aged for 2 hours. A thin layer chromatography plate shows that no starting material is present. The chloroform solution is washed with saturated bicarbonate (3 × 100 ml.) separated and dried (over magnesium sulfate). The solution is filtered and concentrated to an oil (830 mg.). The nmr of this oil indicates the loss of the $\Delta^{1,2}$-double bond and the introduction of the oxirane protons. The crude product is purified by chromatography on silicagel using benzene: 20% ethyl acetate as the elution solvent. Concentration of the appropriate cut gave 700 mg. of the desired compound as an oil.

E. Preparation of 1$\alpha$-Hydroxycholest-5-enol 1,2-Epoxy-$\Delta^5$-cholestene-3$\beta$-ol (130 mg. of 0.00033 moles) prepared according to Example ID above, is dissolved in 40 ml. of dry ether. A suspension of lithium aluminum hydride (80 mg. or 0.0021 moles) in 20 ml. of dry ether is added to this solution with stirring at 0° and refluxed for 4 hours. The reaction mixture is poured into ether containing a 20 ml. of ethyl acetate and shaken with 50 ml. of saturated ammonium chloride solution, and then 50 ml. of water. The organic layer is separated, dried, filtered and evaporated to give a crude product weighing 120 mg. This crude product is chromatographed on silica-gel eluting with benzene: 50% ethyl acetate. Two main cuts are obtained. Concentration of the first cut gives 94 mg. of a white solid, m.p. 158°–160° C. which is 1$\alpha$-hydroxycholest-5-enol.

EXAMPLE 2

Preparation of 1$\alpha$-Hydroxycholest-5-enol

A. Preparation of $\Delta^{1,5}$-Cholestediene-3$\beta$-enol $\Delta^{1,5}$-Cholestediene-3$\beta$-ol (1.2 g or 0.003 moles) is dissolved in 25 ml. of fried, redistilled pyridine; cooled to 0° C. and to this solution acetic anhydride (10 ml.) is added. The reaction mixture is allowed to come to room temperature and aged overnight. A thin layer chromatography plate (in 10% ethyl acetate in benzene) indicates the absence of starting materials. The solution is concentrated under vacuum, added to chloroform (100 ml.), washed 5 times with 100 ml. portions of 2.5N Hydrochloric acid solution, 1 time with 50 ml. of water and 5 times with 100 ml of saturated sodium bicarbonate solution. The organic layer is dried, filtered and concentrated to a golden oil which crystallizes upon cooling. M.P. 79°–81° C.

B. Preparation of $\Delta^5$-Cholestene-1$\alpha$-epoxy-6$\beta$-acetate

The acetate, $\Delta^{1,5}$-cholestediene-3$\beta$-acetate is dissolved in 25 ml. of chloroform. To this solution is added a solution containing 0.71 g. of meta-perbenzoic acid (0.0035 moles) in 25 ml. of chloroform. The mixture is held for one hour, washed with sodium bicarbonate solution (5 times 100 ml.), water (2 times 100 ml.) and dried over magnesium sulfate. The reaction mixture is filtered, the solvent evaporated off and concentrated to an oil (1.39 g.).

C. Preparation of 1$\alpha$-Hydroxycholest-5-enol $\Delta^5$-Cholestene-1$\alpha$,2$\alpha$-epoxy-3$\beta$-acetate, 1.18 g. or 0.002 moles, is dissolved in 100 ml. ether. To this solution with stirring at reflux temperature is added 1.03 g., 0.027 moles, of lithium aluminum hydride. The reaction mixture is refluxed for 4 hours. The excess hydride is removed by adding excess ethyl acetate. The reaction mixture is washed (4 times 250 ml. with saturated ammonium chloride solution), dried over magnesium sulfate, filtered and concentrated under vacuum to give a solid. The crude solid is recrystallized from methanol to give the pure 1$\alpha$-hydroxycholest-5-enol. M.P. 159°–161° C.

Although the process of the instant invention has been illustrated in the foregoing working examples employing starting materials wherein the $R_{24}$ and $R_{25}$ substituents both are hydrogen, it will be obvious to those skilled in the art that compounds wherein $R_{24}$ is methyl and $R_{25}$ is hydrogen or hydroxy and compounds wherein $R_{25}$ is hydroxy and $R_{24}$ is hydrogen or methyl can be prepared merely by substituting the appropriately substituted starting material for that employed in Example 1a.

From a study of the foregoing specification, many obvious modifications in the subject matter of the instant invention will suggest themselves to those skilled in the art. It will be obvious, for example, that the substituent at $R_{24}$, in addition to hydrogen or methyl, could be fluorine and that the substituent at $R_{25}$, in addition to hydrogen or hydroxy, could be fluorine or a $C_{1-5}$ lower-alkyl carbamate. It will be obvious also that acid anhydrides other than acetic anhydride, including, for example, propionic anhydride benzoic anhydride, could be employed to prepare 3-acyloxy compounds of formula VII other than the 3-acetoxy derivative. Applicants consider all such obvious modifications to be the full equivalent of the invention disclosed herein and to fall within the scope of the instant invention.

The subject matter which applicants regard as their invention is particularly pointed out and distinctly claimed as follows:

1. A process for the preparation of a 1α-hydroxycholes-5-enol of the formula:

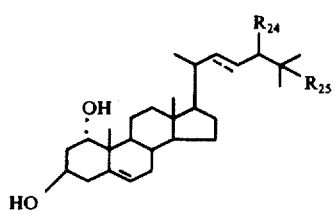

VI wherein $R_{24}$ is a member selected from the group consisting of hydrogen and methyl and $R_{25}$ is a member selected from the group consisting of hydrogen and hydroxy and wherein the dashed line at C-22-23 represents the optional presence of a double bond, which comprises: p1 a. treating $R_{24}$, $R_{25}$-$\Delta^4$-cholestene-3-one of formula I with 2,3-dichloro-5,6-dicyano-1,4-benzoquinone in the presence of a hydrocarbon solvent having a boiling point of about 70° to about 120° C. to produce $R_{24}$, $R_{25}$-$\Delta^{1,4}$-cholestediene-3-one of formula II;

b. rearranging the product of Step (a) with a proton abstracting base to produce $R_{24}$, $R_{25}$-$\Delta^{1,5}$-cholestediene-3-one of formula III;

c. treating the product of Step (b) with a reducing agent capable of reducing a keto group to a hydroxy group to produce $R_{24}$, $R_{25}$-$\Delta^{1,5}$-cholestediene-3β-ol of formula IV;

d. treating the product of Step (c) with an oxidizing agent capable of epoxidizing the 3-hydroxy-$\Delta'$-system to produce $R_{24}$,$R_{25}$,1α, 2α-epoxy-$\Delta^5$-cholestene-3β-ol of formula V; and e. treating the product of Step (d) with a reducing agent capable of reducing the epoxide group to a hydroxy group to produce $R_{24}$,$R_{25}$,1α-hydroxycholest-5-enol of formula VI.

2. A process for the preparation of a 1α-hydroxycholest-5-enol of the formula:

IV

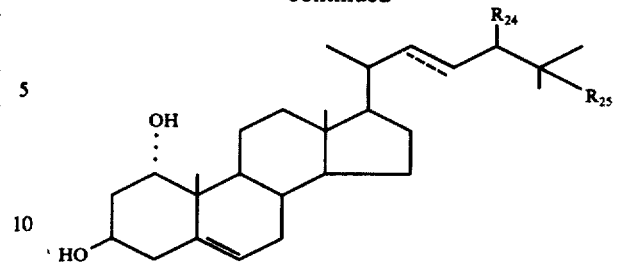

wherein $R_{24}$ is a member selected from the group consisting of hydrogen and methyl and $R_{25}$ is a member selected from the group consisting of hydrogen and hydroxy, and wherein the dashed line at C-22-23 represents the optional presence of a double bond, which comprises:

a. acetylating $R_{24}$,$R_{25}$-$\Delta^{1,5}$-cholestediene-3β-ol of formula IV with acetic anhydride to produce $R_{24}$,$R_{25}$-$\Delta^{1,5}$-cholestediene-3-β-acetate of formula VII;

b. treating the product of Step (a) with an oxidizing agent capable of epoxidizing the 3-hydroxy-$\Delta'$-system to produce $R_{24}$,$R_{25}$,1α,2α-epoxy-$\Delta^5$-cholestene-3β-acetate of formula VIII; and c. treating the product of Step (b) with a reducing agent capable of reducing the epoxide group to a hydroxy group to produce $R_{24}$,$R_{25}$,1α-hydroxycholest-5-enol of formula VI.

3. A 1α,2α-epoxy-$\Delta^5$-cholestene-3β-ol of the formula:

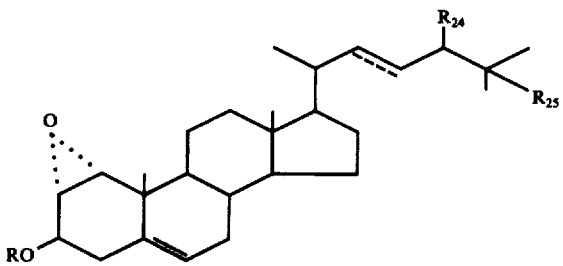

wherein $R_{24}$ is a member selected from the group consisting of hydrogen and methyl, $R_{25}$ is a member selected from the group consisting of hydrogen and hydroxy and R is a member selected from the group consisting of hydrogen and acetyl and wherein the dashed line at C-22-23 represents the optional presence of a double bond.

4. The compound of claim 3 wherein $R_{24}$ and $R_{25}$ are hydrogen.

5. The compound of claim 4 which is 1α-2α-epoxy-$\Delta^5$-cholestene-3β-ol.

6. The compound of claim 4 which is 1α,2α-epoxy-$\Delta^5$-cholestene-3β-acetate.

* * * * *